United States Patent [19]

Rasshofer et al.

[11] Patent Number: 4,665,177

[45] Date of Patent: May 12, 1987

[54] TETRAHYDROPYRIMIDINES, A PROCESS FOR THEIR PRODUCTION AND THEIR USE AS CATALYSTS IN THE PRODUCTION OF POLYURETHANE PLASTICS

[75] Inventors: Werner Rasshofer, Cologne; Gerhard Grögler, Leverkusen; Richard Kopp, Cologne, all of Fed. Rep. of Germany

[73] Assignee: Bayer Aktiengesellschaft, Leverkusen, Fed. Rep. of Germany

[21] Appl. No.: 762,347

[22] Filed: Aug. 5, 1985

Related U.S. Application Data

[63] Continuation-in-part of Ser. No. 332,064, Dec. 18, 1981, abandoned.

[30] Foreign Application Priority Data

Dec. 24, 1980 [DE] Fed. Rep. of Germany ....... 3049131
Dec. 14, 1981 [EP] European Pat. Off. ........ 81110409.0
Dec. 22, 1981 [JP] Japan ................................ 56-206318

[51] Int. Cl.$^4$ ........................................... A61K 403/12
[52] U.S. Cl. ..................................... 544/296; 544/2; 544/5; 544/8; 544/55; 544/60; 544/66; 544/65; 544/67; 544/96; 544/122; 544/182; 544/238; 544/295; 544/242; 544/322; 525/457
[58] Field of Search ..................... 544/296, 2, 5, 8, 55, 544/60, 65, 66, 67, 96, 122, 182, 238, 295, 242, 322

[56] References Cited

U.S. PATENT DOCUMENTS 3,549,592 12/1970 Godfrey et al. ....................... 260/47
3,674,721 7/1972 Aufdermarsh, Jr. et al. ....... 260/2.5 AC
4,150,212 4/1979 Meyborg ............................... 528/52

FOREIGN PATENT DOCUMENTS 2154948 3/1973 Fed. Rep. of Germany.
2737671 2/1979 Fed. Rep. of Germany.
7102672 1/1971 Japan.
1182014 2/1970 United Kingdom.

OTHER PUBLICATIONS

Catalysis in Isocyanate Reactions-J. Macromol Sci. Revs. Macromol Chem. Soc. C5 (1) 103-150.
J. Chem. Soc. 1947 (497).
J. Amer. Chem. Soc. 71 2350 (1949).
Chem. Ber. 98, 3652 (1965).
Synthesis, 1972, No. 1, p. 37.

Primary Examiner—Glennon H. Hollrah
Assistant Examiner—James H. Turnipseed
Attorney, Agent, or Firm—Gene Harsh; Joseph C. Gil; Lyndanne M. Whalen

[57] ABSTRACT

This invention relates to new tetrahydropyrimidines, to a process for their production and to their use as catalysts in the production of polyurethane plastics, including polyurethane foams.

6 Claims, No Drawings

TETRAHYDROPYRIMIDINES, A PROCESS FOR THEIR PRODUCTION AND THEIR USE AS CATALYSTS IN THE PRODUCTION OF POLYURETHANE PLASTICS

CROSS-REFERENCE TO RELATED APPLICATION

The present application is a continuation-in-part of U.S. application Ser. No. 332,064, filed Dec. 18, 1981, now abandoned.

BACKGROUND OF THE INVENTION

This invention relates to new tetrahydropyrimidines, to a process for their production and to their use as catalysts in the production of polyurethane plastics, including polyurethane foams.

Numerous amines have already been used as catalysts in the production of polyurethanes by reacting polyols with polyisocyanates (see, K. C. Frisch, L. P. Rennao, "Catalysis in Isocyanate Reactions" in J. Macromol. Sci.–Revs. Macromol. Chem. Soc. C 5 (1), 103–150).

In the case of the most active amines which are generally tertiary amines, for example, 1,4-diazabicyclo-(2.2.2)-octane (triethylenediamine, Dabco ®), concentrations of from 0.04 to 0.5 parts by weight, based on the polyol used, are necessary. Other amines have to be used in considerably larger quantities, as is the case where aliphatic isocyanates are used.

However, these small quantities of amine catalyst often involve serious disadvantages. Since the amines used are generally tertiary amines which cannot be incorporated, an unpleasant odor is still in evidence some time after production. This applies in particular to articles of everyday use, such as upholstery, motor vehicle fittings, shoes and furniture. Also, these amines are frequently responsible for the yellowing of light-colored leather or plastics surfaces.

Another disadvantage of non-incorporable amine catalysts of the type in question is that they often have a tendency to exude to the surface by other physical and/or chemical processes. Thus, a white coating in which diazabicycloundecene is found can be formed, for example, on a diazabicycloundecene-catalyzed polyurethane material of the type used in the production of steering wheels and headrests. Similarly, where triethylene diamine is used as catalyst in the production of polyurethane shoe soles, discoloration is frequently observed in light-colored upper leathers, making it impossible for the sole to be directly foamed onto the shoe upper. This discoloration is produced by triethylene diamine escaping during the foaming reaction. A similar effect is observed where non-incorporable tetrahydropyrimidines are used as catalyst.

Acyclic amidines as catalysts in the production of polyurethanes from aliphatic isocyanates are described in German Offenlegungsschrift No. 1,950,262. German Offenlegungsschrift No. 2,737,671 describes the use of combinations of cyclic amidines, which have tetrahydropyrimidine or imidazoline structures, and metal salts as catalysts for the production of polyurethanes.

Published Japanese Patent Application No. 7,102,672 describes the use of tetrahydropyrimidines for catalyzing urethanization reactions. Bicyclic amidines as polyurethane catalysts are described in German Offenlegungsschrift No. 1,745,418.

However, these catalysts still do not meet the practical needs for high catalytic activity and odorlessness of the plastics material obtained.

German Offenlegungsschrift No. 2,601,082 already describes the production of polyurethanes using incorporable catalysts of the amidine type. However, the aminopyridines mentioned in that reference show only sufficient catalytic activity for the production of polyurethanes from aromatic polyisocyanates, being too weak for the production of polyurethanes from aliphatic polyisocyanates. Accordingly, the scope of application of aminopyridines as catalysts in the production of polyurethanes is often too narrow for practical purposes.

Now, it is surprisingly possible by virtue of the present invention to overcome the disadvantages shown from the prior art. The tetrahydropyrimidines disclosed and used in accordance with the invention are excellent catalysts for the production of polyurethanes both from aliphatic and also from aromatic polyisocyanates.

Also, the polyurethane plastics produced with them show no noticeable amine odor.

The tetrahydropyrimidines according to the invention have a very much lower vapor pressure than the cyclic amidines according to German Offenlegungsschrift No. 1,950,262, the bicyclic amidines according to German Offenlegungsschrift No. 2,737,671 and the tetrahydropyrimidines according to Japanese Patent Application No. 7,102,672.

In addition, as catalysts:

1. In general, they are highly compatible with the PU-matrix;
2. In many cases, they have a particularly high content of catalytically active groups in the molecule; and
3. They are more stable to hydrolysis than the hitherto known monocyclic tetrahydropyrimidines.

There are already numerous other processes for the production of 1-alkyl-2-methyl-tetrahydropyrimidines, including, for example, the reaction of N-alkyl propylene diamines with open-chain imido acid esters or amidines (A. Pinner, Die Chemie der Imidoether und ihrer Derivate (The Chemistry of the Imido Ethers and Their Derivatives), R. Oppenheim, Berlin, 1892); the reaction of N-alkyl propylene diaminotoluene sulfonic acid salts with carboxylic acid nitriles (J. Chem. Soc. 1947, 497); the hydrogenation of N-acylaminonitriles with the N-acyl-N-alkylpropylene diamines formed being dehydrated under the reaction conditions to form 1-alkyl-2-methyl tetrahydropyrimidines (J. Am. Chem. Soc. 71, 2350 (1949)); and the reaction of N-alkyl propylene diamines with oxazolines (DE-OS No. 2,154,948). However, many of these processes have the disadvantage that the reaction is not complete and, in particular, large quantities of unwanted secondary products are formed. The reaction temperature in all these processes is in the range of from 100° to 200° C., the reaction being carried out in the presence of catalysts, for example, acid compounds (e.g., hydrochloric acid or toluene sulfonic acid) or metal compounds (e.g., Ni, Co or Cu).

The reaction, as described in Chem. Ber. 98, 3652 (1965), of N-ethyl propylene diamine with acetoacetic acid ethyl ester in the presence of toluene sulfonic acid at high reaction temperatures of 210° C. is also known. This process is described with reference to a 0.2 molar reaction batch which unfortunately cannot be scaled up to industrial levels.

As cyclic amidines, tetrahydropyrimidines are extremely sensitive to hydrolysis. At the temperature mentioned and in the presence of acid compounds such as toluene sulfonic acid, the cyclic amidine is immediately hydrolyzed by the water formed during the condensation reaction. The N-acyl-N-ethyl propylene diamine formed by hydrolysis may be slowly recycled with elimination of water under the conditions prevailing during working up by distillation, and this may be done in an entirely acceptable time in the case of a 0.2 molar batch but, where this process is carried out commercially with batches of 100 kg and larger, this leads to a completely unsatisfactory volume-time yield. Working up of the ternary mixture which accumulates, consisting of tetrahydropyrimidine, its hydrolysis product N-acyl-N-alkyl propylene diamine and water is extremely complicated and requires a time-consuming and complex distillation process. In addition, a very high percentage of unusable residues is obtained in consequence of the thermal stressing of the reaction mixture, significantly reducing the yield of pure product.

In addition, the production of N-substituted tetrahydropyrimidines from N-alkyl propane diamines and $\Delta^2$-oxazolines in commercially inadequate yields of 19 to 73% is described in Synthesis 1972, No. 1, page 37.

Accordingly, another object of the present invention is to develop a process which enables tetrahydropyrimidines corresponding to general formulae disclosed below to be obtained in high yields and in high degrees of purity.

DESCRIPTION OF THE INVENTION

Accordingly, the present invention relates to new tetrahydropyrimidines corresponding to the formula $$\text{(I)}$$

wherein
A is a divalent straight-chain or branched-chain $C_1$-$C_{17}$-alkylene or $C_5$-$C_{10}$-cycloalkylene radical which may be interrupted in the chain by —NH—COO—, —O— and/or —S—; or a $C_1$-$C_4$ alkylene bis(cyclohexyl) radical which may be substituted by a phenyl or halogen radical or a cyano group; or a dicyclohexyl radical;

X is a monovalent straight-chain or branched-chain $C_1$-$C_{16}$-alkyl radical; a $C_5$-$C_7$-cycloalkyl radical which may be substituted by a phenyl or halogen radical or a cyano or hydroxy group; or, where h=0, together with N may form a ring consisting of 3 to 6 ring-C-atoms of which one or two C-atoms may be replaced by —O—, —S—, —NH— or —NR$^3$— where R$^3$ represents a $C_1$-$C_6$-alkyl or ω-hydroxy-$C_1$-$C_6$-alkyl;

a=0 or an integer of from 1 to 16;

b=an integer of from 1 to 16, but if d=0, then b must=0;

c=1 or 2, but if d=0, then c must=0;

d=0 or an integer of from 1 to 10;

e=0 or 1, but if g=0, then e must=0;

f=0 or an integer of from 1 to 16, but if g=0, then f must=0;

g=an integer of from 1 to 16, but if h=0, then g must=0;

h=0 or 1, but if d≧1, then h+c must=2; and d and h cannot both=0.

According to the invention, preferred tetrahydropyrimidines are the new tetrahydropyrimidines corresponding to the formula $$\text{(II)}$$

wherein
A is a divalent straight-chain or branched-chain $C_1$-$C_{17}$-alkylene or $C_5$-$C_{10}$-cycloalkylene radical which may be interrupted in the chain by —NH—COO—, —O— and/or —S—; or a $C_1$-$C_4$ alkylene bis(cyclohexyl) radical which may be substituted by a phenyl or halogen radical or a cyano group; or a dicyclohexyl radical;

a and f are 0 or integers of from 1 to 16; and e is 0 or 1.

According to the invention, other preferred tetrahydropyrimidines are the new tetrahydropyrimidines corresponding to the formula $$\text{(III)}$$

wherein
X represents a straight-chain or branched-chain $C_1$-$C_{16}$-alkyl radical or a $C_5$-$C_7$-cycloalkyl radical which may be substituted by a phenyl radical, a cyano group or a halogen radical;

m and p are integers of from 2 to 10; and n is an integer of from 1 to 16.

According to the invention, other preferred tetrahydropyrimidines correspond to formula IV below:

$$\text{(IV)}$$

wherein
m is an integer of from 2 to 10; and

R$^1$ and R$^2$ independently of one another represent a straight-chain or branched-chain $C_1$-$C_{10}$-alkyl radical or a $C_5$-$C_7$-cycloalkyl radical which may be substituted by a phenyl radical, a cyano group, a hydroxyl group or a halogen atom, or together form a ring consisting of 3 to 6 ring-C-atoms of which one or two C-atoms may be replaced by —O—, —S—, —NH— or —NR³— where R³ is a C₁-C₆-alkyl or ω-hydroxy-C₁-C₆-alkyl radical.

To modify the catalytic activity of the compounds according to the invention containing tetrahydropyrimidine units, it is often advantageous to use them in the form of their salts, addition compounds and complexes. To this end, it is possible to use proton donors, such as organic or inorganic acids, and other acid compounds. It is possible, in principle, to use any compound of which the base strength is lower than that of the tetrahydropyrimidines.

In addition, it is possible to use Lewis acids which react as coordinatively unsaturated compounds with electron donors. This modification also leads in part to further increased protection against hydrolysis for the compounds according to the invention containing tetrahydropyrimidine units.

Accordingly, the present invention also relates to salts, addition compounds and complexes of the tetrahydropyrimidines according to the invention with proton acids and Lewis acids.

The present invention also relates to a process for the production of tetrahydropyrimidines corresponding to the formula (I) above by reacting N-substituted propyylene diamines corresponding to the formula

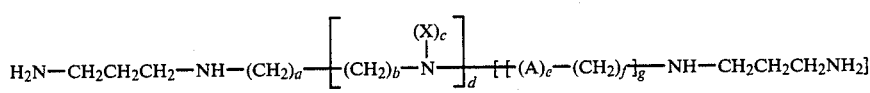

wherein
A, X, a, b, c, d, e, f, g and h are as defined above, with acetoacetic acid derivatives corresponding to the formula

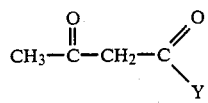   (VI)

wherein
Y represents —OR³, —NHR³ or —NH³₂; and
R³ is a C₆–C₁₀-aryl, C₁–C₁₇-alkyl or a C₅–C₇-cycloalkyl radical, the reaction being conducted in the absence of catalysts at a reaction temperature in the range from 0° to 80° C. and the water formed during the reaction being continuously removed.

The present invention also relates to a process for the production of tetrahydropyrimidines corresponding to the formula (II) above by reacting N-substituted bis-propylene diamines corresponding to the formula

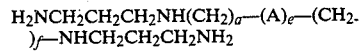

in which
A, a, e and f are as defined above, with acetoacetic acid derivatives corresponding to formula (VI) above in the absence of catalysts at a reaction temperature in the range from 0° to 80° C. and the water formed during the reaction being continuously removed.

The present invention also relates to a process for the production of tetrahydropyrimidines corresponding to formula (III) above by reacting N-substituted bis-propylene diamines corresponding to the formula

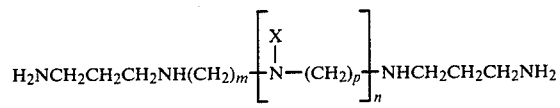

in which
X, m, n and p are as defined above, with acetoacetic acid derivatives corresponding to formula (VI) above in the absence of catalysts at a reaction temperature in the range from 0° to 80° C. and the water formed during the reaction is continuously removed.

The present invention also relates to a process for the production of tetrahydropyrimidines corresponding to formula (IV) above by reacting N-substituted bis-propylene diamines corresponding to the general formula

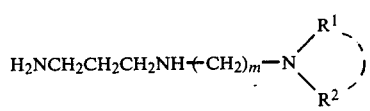

in which
m, R¹ and R² are as defined above, with acetoacetic acid derivatives corresponding to formula (VI) above in the absence of catalysts at a reaction temperature in the range from 0° to 80° C. and the water formed during the reaction is continuously removed.

Finally, the present invention also relates to the use of the various tetrahydropyrimidines described herein as catalysts in the production of polyurethane plastics. The polyurethanes are produced by reacting polyisocyanates with compounds containing at least two isocyanate-reactive hydrogen atoms and having molecular weights in the range from 400 to 10,000 in the presence of these catalysts and optionally in the presence of compounds containing at least two isocyanate-reactive hydrogen atoms and having molecular weights in the range of from 32 to 400 as chain-extending agents, and optionally blowing agents and other auxiliaries and additives.

It has been found that the process described in German Auslegeschrift No. 2,439,550 for the production of tetrahydropyrimidines corresponding to the formula

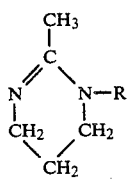

wherein
R is a straight-chain, alkyl-branched or cyclic, saturated aliphatic hydrocarbon radical containing 1 to 17 carbon atoms which may be substituted by a phenyl radical, a cyano group or a halogen atom, may also be used for producing the tetrahydropyrimidine compounds according to the invention.

One process of the present invention comprises reacting specific N-substituted compounds containing two propylene diamine units with specific acetoacetic acid derivatives in the absence of catalysts at a reaction temperature in the range from 0° to 80° C. and continuously removing the water formed during the reaction from the circuit.

The process gives the required products in generally high purity and in high yields, the reaction being regioselective. This is surprising insofar as the number of reactive centers is increased by comparison with the process known from German Auslegeschrift No. 2,439,550 so that there is an increase in probability of the production of products other than the required products as a result of the possible intermolecular and intramolecular reactions.

The N-substituted amines having 1,3-diaminopropane units at both ends, which may be used in the process according to the invention, are known and are generally of the type obtained by reacting acrylonitrile with 1,-diamines, followed by reduction. Suitable 1,-diamines include, for example, 1,2-diaminoethane; 1,4-diaminobutane; 1,6-diaminohexane: 1,12-diaminododecane 1,5-diamino-3-oxapentane 1,8-diamino-3,6-dioxaoctane: 3-methyl-3-aza-1,5-diaminopentane 1,8-diamino-3-methyl-3-azaoctane; 1-aminomethyl-5-amino-1,3,3-trimethyl cyclohexane; 1,4-diaminocyclohexane; hydrolysis products of NCO-prepolymers, of the type obtained by reacting aliphatic polyisocyanates with polyhydroxy compounds in an NCO:OH molar ratio of 2:1; and also the following compounds

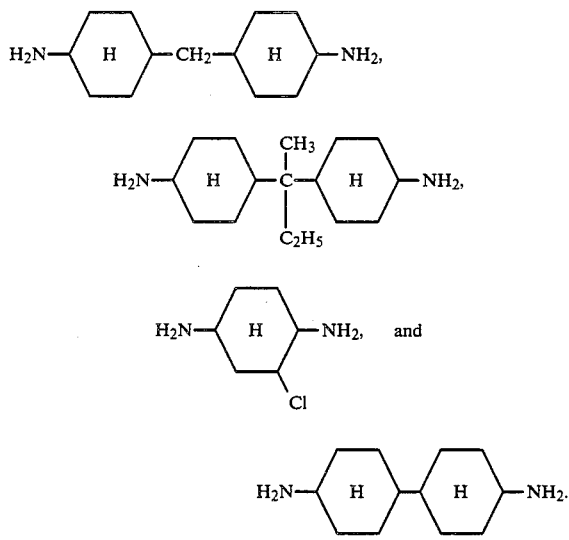

Acetoacetic acid derivatives suitable for use in the process according to the invention are acetoacetic acid esters and mono- or di-substituted acetoacetic acid amides. Preferred acetoacetic acid derivatives are those within the scope of the aforesaid formula (VI), and those esters (Y=OR$^3$) in which R$^3$ represents a saturated $C_1$-$C_6$-alkyl or $C_5$-$C_6$-cycloalkyl radical are particularly preferred. Examples of suitable acetoacetic acid derivatives include: acetoacetic acid methyl ester, acetoacetic acid ethyl ester, acetoacetic acid butyl ester, acetoacetic acid benzyl ester, acetoacetic acid phenyl ester, acetoacetic acid N-methylamide, acetoacetic acid N-diethylamide, acetoacetic acid N-butylamide, acetoacetic acid N-dipropylamide, acetoacetic acid N-benzylamide, acetoacetic acid N-cyclohexylamide, acetoacetic acid N-phenylamide.

The acetoacetic acid derivatives suitable for use in the process according to the invention may readily be obtained in known manner by reacting diketene with the corresponding alcohols or N-mono- or N-di-substituted amines.

Either the N-substituted propylene diamine is introduced into the acetoacetic acid derivative or the acetoacetic acid derivative is introduced into the N-substituted propylene diamine. The reaction may then be carried out in the presence or absence of a solvent (preferably in the presence of a solvent which is inert to the starting and reaction products and from which the water formed during the reaction may be distilled azeotropically) at a temperature in the range from 0° to 80° C. (preferably adjusted to between 10° and 70° C. and, with particular preference to between 20° and 50° C.). The water formed during the reaction is removed at 0° to 80° C. by adding a water-removing agent which is inert to the starting and reaction products; by distillation, optionally under reduced pressure; or by azeotropic distillation, optionally under reduced pressure. Working up of the residual reaction mixture to obtain 1-substituted 2-methyl tetrahydropyrimidine is carried out in known manner, for example by distillation or extraction.

The starting compounds are best used in a 1:1 molar ratio, but it may be of advantage to use one of the starting compounds in excess, for example in an excess of up to 1.5 moles per mole of the second starting compound.

The reaction is preferably carried out in the presence of a solvent. The solvent should best be inert to the starting and reaction products. Examples of suitable solvents are halogenated hydrocarbons, aromatic hydrocarbons, esters and ethers. It is preferred to use inert solvents of the type with which the water formed during the reaction may also be subsequently distilled off azeotropically.

It is possible with advantage to use inert solvents of the type which boil below 150° C. under normal pressure and which form an azeotrope with water, such as halogenated hydrocarbons and aromatic hydrocarbons. Specifically, dichloromethane, trichloromethane, benzene, toluene, xylene and chlorobenzene possess these properties.

The reaction temperature in the process according to the invention is preferably adjusted to between 10° and 70° C. and, with particular preference, to between 20° and 50° C. The water formed in the process according to the invention is preferably removed at 10° to 70° C. and, with particular preference, at 20° to 50° C. As already mentioned, the water may be removed for example by distillation, azeotropic distillation or by the addition of an inert water-removing agent.

If the water of reaction is removed by distillation, distillation is preferably carried out in vacuo (for example, at pressures between 10 and 700 Torr) so that the temperatures may be kept below 80° C. during removal of the water. Where the water of reaction is to be removed by the addition of an inert water-removing agent, such as anhydrous soda, zeolites, barium oxide or calcium oxide, that agent is best added in excess of that quantity to which the theoretically calculated quantity of water formed can be bound.

The water is preferably removed by azeotropic distillation using one of the already described azeotrope-forming solvents. Where the azeotropic distillation process is carried out in batches, the azeotrope-forming solvent is best added in excess of that quantity from which the theoretically calculated quantity of water of reaction formed can be removed. Where the azeotropic distillation process is carried out continuously, it is possible to use even less azeotrope-forming solvent. In azeotropic distillation, the aquepus phase is removed after cooling and phase separation of the azeotrope which has been distilled off, and the azeotrope-forming solvent is recycled. This circuit may be maintained until no more water is discharged from the reaction mixture. The pressure conditions to be maintained during removal of the water of reaction by azeotropic distillation depend upon the azeotrope formed and are selected in such a way that the temperature (of the reaction mixture) does not rise above 80° C. during the azeotropic distillation step. Where azeotropes which boil below 80° C. under normal pressure are formed, it is possible to work under normal pressure or reduced pressure. In this case, suitable pressures are for example pressures from 10 Torr to atmospheric pressure and, more particularly, pressures from 15 to 50 Torr. Where azeotropes boiling above 80° C. under normal pressure are formed, it is necessary to work under reduced pressure. Suitable pressures in this case are, for example, pressures in the range from 10 to 200 Torr and, more particularly, pressures in the range from 15 to 50 Torr.

The tetrahydropyrimidine is preferably recovered from the reaction mixture obtained by distillation. The pressure under which this distillation step is carried out may be varied within wide limits because the temperature may now even rise to above 80° C. without secondary reactions taking place to any significant extent. For example, it is possible to apply such pressures that the tetrahydropyrimidine to be separated off boils anywhere between 0° and 300° C. It is preferred to work under normal pressure or a reduced pressure, such as in the range of from 0.01 to 760 Torr. Pressures of from about 0.1 to 50 Torr and a boiling temperature of the tetrahydropyrimidine to be separated off in the range of from 100° to 300° C. are particularly preferred.

Also, whereas the process according to Chem. Ber. 98, 3652 (1958) is carried out at high temperatures and in the presence of toluene sulfonic acid as catalyst, the water of reaction remaining in the reaction mixture for a relatively long time, the process according to the invention is based on the fundamental observation that high yields of 1-substituted 2-methyl tetrahydropyrimidines are only obtained when low temperatures are applied and no catalyst is used. In addition, it has been found that the water of reaction has to be removed from the reaction mixture at a low temperature to prevent hydrolysis of the cyclic amidine.

The tetrahydropyrimidines thus produced may be readily obtained in high yields on an industrial scale and the process according to the invention may be carried out continuously without any difficulty.

Typical proton donor compounds or proton acids for the production of addition compounds, salts and complexes with the tetrahydropyrimidine compounds according to the invention include, for example, monocarboxylic acids, such as formic, acetic, propionic, butyric, caproic, valeric, octylic, lauric, stearic and oleic acids; dicarboxylic acids, such as oxalic, malonic, succinic, fumaric and adipic acids; hydroxy acids, such as glycolic, lactic and tartaric acids; sulfonic acids, such as alkyl or aryl sulfonic, sulfamic and sulfanilic acids; inorganic acids, such as carbonic, phosphoric, hydrochloric and sulfuric acids; and other proton donor compounds, such as sulfonamides; phenols, such as phenol and cresol; and enols, such as barbituric acid and uric acid. Fatty acids containing at least two carbon atoms, phenols and carbonic acid are particularly preferred.

To produce the "acid addition salts", the free base is merely reacted with a stoichiometric quantity of the proton donor compounds selected, with salt formation taking place easily at room temperature without the assistance of a catalyst. In cases where solid reactants are used, it may be of advantage to use an inert, liquid solvent, such as benzene, toluene, xylene, hexane, heptane, dichloromethane or trichloromethane which may readily be removed by conventional processes on completion of the reaction as the reaction medium. There is no need for further purification of the "acid addition salt", although recrystallization from a solvent such as iso-octane may be applied if a product of high purity is required.

Lewis acids such as $SO_2$, $SO_3$, $BF_3$, $BCl_3$, $BI_3$, $Al_2Cl_6$, $SnCl_4$, which are known in the broad sense to be electron-deficient compounds (see "Anorganische Chemie (Inorganic Chemistry)" by F. A. Cotton and G. Wilkinson, 2nd Edition, Verlag Chemie GmbH, Weinheim/Bergstrasse 1968, or in the textbook by Edwin S. Gould entitled "Mechanismus und Struktur in der Organischen Chemie" (Mechanism and Structure in Organic Chemistry), 2nd Edition, Verlag Chemie GmbH, Weinheim/ Bergstr., 1969) may be used to further modify the compounds according to the invention to increase their resistance to hydrolysis.

According to the invention, the following tetrahydropyrimidines are preferred:

1,2-bis-(2-methyl-tetrahydropyrimidinoyl-1)-ethane corresponding to the following formula

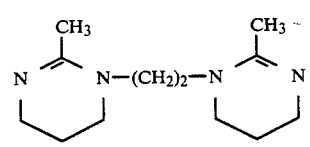

1,4-bis-(2-methyl-tetrahydropyrimidinoyl-1)-butane corresponding to the following formula

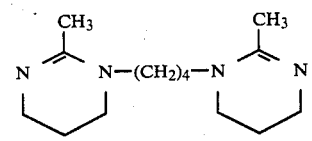

1,6-bis-(2-methyl-tetrahydropyrimidinoyl-1)-hexane corresponding to the following formula

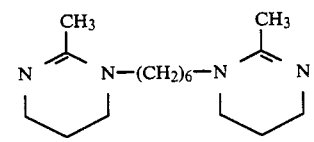

1,5-bis-(2-methyl-tetrahydropyrimidinoyl-1)-3-oxapentane corresponding to the following formula

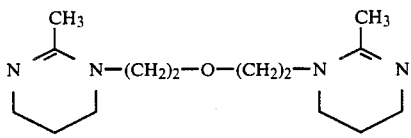

1,8-bis-(2-methyl-tetrahydropyrimidinoyl-1)-3,6-dioxaoctane corresponding to the following formula

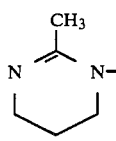

1,9-bis-(2-methyl-tetrahydropyrimidinoyl-1)-5-oxanonane corresponding to the following formula

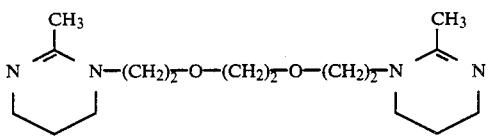

1,5-bis-(2-methyl-tetrahydropyrimidinoyl-1)-3-methyl-3-azapentane corresponding to the following formula

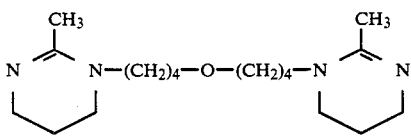

1,5-bis-(2-methyl-tetrahydropyrimidinoyl-1)-3-n-dodecyl-3-azapentane corresponding to the following formula

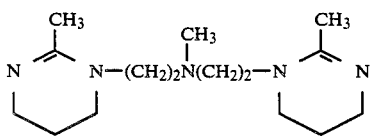

1,8-bis-(2-methyl-tetrahydropyrimidinyoyl-1)-3,6-dimethyl-3,6-diazaoctane corresonding to the following formula

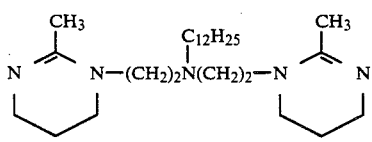

1,7-bis-(2-methyl-tetrahydropyrimidinoyl-1)-4-methyl-4-azaheptane corresponding to the following formula

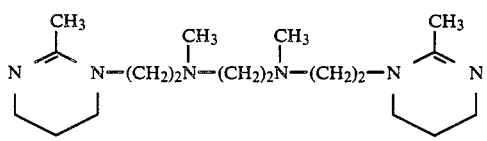

1,23-bis-(2-methyl-tetrahydropyrimidinoyl-1)-10,14-dimethyl-8,16-dioxo-7,17-diaza-9,12,15-trioxa-tricosane corresponding to the formula (idealized)

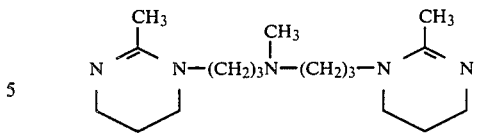

1-(3-di-N-methylaminopropyl)-2-methyl-tetrahydropyrimidine corresponding to the following formula

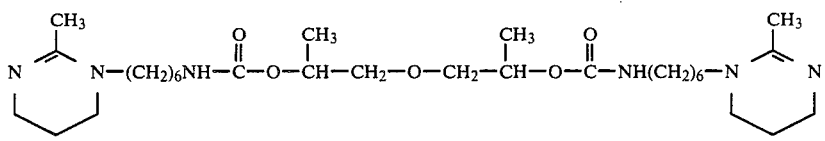

and their salts, addition compounds and complexes with proton and Lewis acids. 1,5-bis-(2-methyl-tetrahydropyrimidinoyl-1)-3-oxapentane and 1,7-bis-(2-methyl-tetrahydropyrimidinoyl-1)-4-methyl-4-azaheptane are particularly preferred.

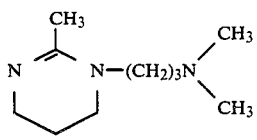

The tetrahydropyrimidines according to the invention are low-melting or liquid compounds which, in general, are highly soluble in the high molecular weight or low molecular weight polyhydroxyl compounds used for the production of polyurethane foams. However, the tetrahydropyrimidine component may also be used in finely dispersed form.

The catalysts according to the invention containing tetrahydropyrimidine units are odorless or have a weak, pleasant odor - not the typical unpleasant "amine odor".

Suitable starting materials for the production of the polyurethane plastics are organic polyisocyanates of the type described in German Offenlegungsschrift No. 2,854,384, page 8, line 13 to page 11, line 20. Reactants for these polyisocyanates are compounds containing at least two isocyanate-reactive hydrogen atoms and having a molecular weight in the range from 400 to 10,000, of the type disclosed in detail in German Offenlegungsschrift No. 2,854,384, page 11, line 21 to page 19, line 29. Compounds containing at least two isocyanate-reactive hydrogen atoms and having a molecular weight in the range from 32 to 400 are optionally used as chain-extending agents and crosslinking agents in the production of the polyurethane plastics. Compounds of this type are described for example in German Offenlegungsschrift No. 2,854,384, page 20, line 1 to page 26, line 5. In addition, blowing agents and other auxiliaries and additives may optionally be used. Suitable blowing agents and auxiliaries and additives are described in German Offenlegungsschrift No. 2,854,384, page 26, line 6 to page 31, line 17.

The catalysts according to the invention are used in quantities of from 0.01 to 10% by weight, preferably in quantities of from 0.05 to 5% by weight and, with particular preference, in quantities of from 0.1 to 2% by weight, based on the quantity in which the compounds containing at least two active hydrogen atoms and having a molecular weight in the range from 400 to 10,000 are used.

The tetrahydropyrimidine catalysts according to the invention are preferably used in combination with other catalysts known from polyurethane chemistry, preferably amine-containing and metal catalysts, at least 2% by weight and preferably at least 20% by weight of the total quantity of catalyst used consisting of the tetrahydropyrimidine catalysts according to the invention.

Examples of catalysts which may be used in addition to the catalysts according to the invention are tertiary amines, such as triethyl amine, tributyl amine, N-methyl morpholine, N-ethyl morpholine, N,N,N'N'-tetramethyl ethylene diamine, pentamethyl diethylene triamine and higher homologs (German Offenlegungsschrift Nos. 2,624,527 and 2,624,528), 1,4-diazabicyclo-(2,2,2)-octane, N-methyl-N'-dimethylaminoethyl-piperazine, bis-(dimethylaminoalkyl)-piperazines (German Offenlegungsschrift No. 2,636,787), N,N-dimethyl benzylamine, N,N-dimethylcyclohexylamine, N,N-diethylbenzylamine, bis-(N,N-diethylaminoethyl)-adipate, N,N,N',N'-tetramethyl-1,3-butane diamine, N,N-dimethyl-β-phenylethylamine, 1,2-dimethyl imidazole, 2-methyl imidazole, monocyclic and bicyclic amidines (German Offenlegungsschrift No. 1,720,633), bis-(dialkylamino)-alkyl ethers (U.S. Pat. No. 3,330,782, German Auslegeschrift No. 1,030,558 and German Offenlegungsschrift Nos. 1,804,361 and 2,618,280) and tertiary amines containing amide groups (preferably for amide groups) according to German Offenlegungsschrift Nos. 2,523,633 and 2,732,292. Other suitable additional catalysts are known Mannich bases of secondary amines, such as dimethyl amine; and aldehydes, preferably formaldehyde; or ketones, such as acetone, methyl ethyl ketone or cyclohexanone; and phenols, such as phenol, nonyl phenol or bisphenol. Tertiary amines containing isocyanatereactive hydrogen atoms suitable for use as additional catalysts are, for example, triethanolamine, triisopropanolamine, N-methyl diethanolamine, N-ethyl diethanolamine, N,N-dimethyl ethanolamine, their reaction products with alkylene oxides, such as propylene oxide and/or ethylene oxide, as well as secondary-tertiary amines according to German Offenlegungsschrift No. 2,732,292. Other suitable additional catalysts include sila-amines containing carbon-silicon bonds of the type described, for example, in German Pat. No. 1,229,290 (corresponding to U.S. Pat. No. 3,620,984), for example, 2,2,4-trimethyl-2-silamorpholine and 1,3-diethylaminomethyl tetramethyl disiloxane; nitrogen-containing bases, such as tetra-alkyl ammonium hydroxides; alkali hydroxides, such as sodium hydroxide; alkali phenolates, such as sodium phenolate; alkali alcoholates, such as sodium methylate or hexahydrotriazines (German Offenlegungsschrift No. 1,769,043). The reaction between NCO-groups and Zerewitinoff-active hydrogen atoms is also greatly accelerated by lactams and azalactams, an associate between the lactam and the compound containing acid hydrogen initially being formed. Associates such as these and their catalytic acitivity are described in German Offenlegungsschrift Nos. 2,062,288; 2,062,289; 2,117,576 (U.S. Pat. No. 3,758,444); 2,129,198; 2,330,175; and 2,330,211.

According to the invention, organometallic compounds, particularly organotin compounds, organic lead compounds and organic bismuth compounds, may also be used as additional catalysts. In addition to sulfur-containing compounds, such as di-n-octyl tin mercaptide (German Auslegeschrift No. 1,769,367; U.S. Pat. No. 3,645,927), preferred organo tin compounds are tin(II) salts of carboxylic acids, such as tin(II)acetate, tin(II)octoate, tin(II)ethyl hexoate and tin(II)laurate, and tin(IV)compounds, for example dibutyl tin oxide, dibutyl tin dichloride, dibutyl tin diacetate, dibutyl tin dilaurate, dibutyl tin maleate or dioctyl tin diacetate, lead compounds, such as Pb(II)octoate, and bismuth compounds, such as Bi(III)-octoate or Bi(III)-thiododecylate.

All of these catalysts mentioned above may, of course, be used in the form of mixtures. Combinations of organometallic compounds and amidines, aminopyridines or hydrazinopyridines (German Offenlegungsschrift Nos. 2,434,185, 2,601,082 and 2,603,834) are of particular interest.

These additional catalysts are generally used in a quantity of from about 0.001 to 10% by weight, based on the total quantity of compounds containing at least two isocyanate-reactive hydrogen atoms and having a molecular weight in the range of from 400 to 10,000, and in quantities of from 0 to 98% by weight and preferably in quantities of from 0 to 80% by weight, based on the total quantity of catalysts used.

These same conditions apply to the salts, addition compounds and complexes of the tetrahydropyrimidines according to the invention. However, where these salts, addition compounds and complexes are used in combination with co-catalysts of the type mentioned above, it is important to ensure that no exchange reactions which could destroy the required effect take place between the components of the catalyst.

A particular embodiment of the production of polyurethane plastics in accordance with the invention is characterized in that the catalysts used are carbonates and hydrogen carbonates of the new tetrahydropyrimidines, optionally in admixture with other hydrogen carbonates and carbonates of known amine and amidine catalysts, and in that no other physical blowing agents are used (the new tetrahydropyrimidine salts acting as both catalysts and blowing agents).

In the production of the polyurethane plastics according to the invention, the reaction components are reacted by the known one-shot process, by the prepolymer process or by the semi-prepolymer process, in many cases using machines, for example, of the type described in U.S. Pat. No. 2,764,565 or in Kunststoff-Handbuch by Vieweg and Hochtlen, Vol. VII, Carl-Hanser-Verlag, Munich, 1966, for example, on pages 121 to 205.

In the production of foams, it is also possible in accordance with the invention to carry out foaming in closed molds. To this end, the foamable reaction mixture is introduced into a mold made of suitable materials, such as metals, including aluminum, or plastics, including epoxide resin, foams in the mold and forms the molding. In-mold foaming may be carried out in such a way that the molding has a cellular structure at its surface, although it may also be carried out in such a way that the molding has a compact skin and a cellular core. The foamable reaction mixture may be introduced into the mold in such a quantity that the foam formed just fills the mold or more foamable reaction mixture than is required for filling the interior of the mold with foam may be introduced into the mold (this latter technique being known as overcharging and shown, for example, in U.S. Pat. Nos. 3,178,490 and 3,182,104).

In many cases, known "external release agents", such as silicone oils, are used for in-mold foaming. However, it is also possible to use so-called "internal release agents", optionally in admixture with external release agents, of the type known for example from German Offenlegungsschrift Nos. 2,121,670 and 2,307,589.

According to the invention, it is also possible to produce cold-hardening foams (see British Pat. No. 1,162,517 and German Offenlegungsschrift No. 2,153,086) and to produce foams by block foaming or by the known laminator process.

The products obtainable in accordance with the invention may be used for example as shoe soles, upholstery material, sound insulating materials, coating materials, lacquers, packaging materials and mattresses.

The invention is further illustrated, but is not intended to be limited by the following examples in which all parts and percentage are by weight unless otherwise specified.

EXAMPLES

EXAMPLE 1

Production of 1,2-bis-(2-methyl-tetrahydropyrimidinoyl-1)-ethane 174 g (1 mole) of 1,10-diamino-4,7-diazadecane, 260 g (2 moles) of acetoacetic ester and 250 ml of toluene are combined and kept for 2 hours at an internal flask temperature of 40° C. and under a pressure of 20 Torr, with 36 g of water (100%) being separated off in an evacuable water separator. On completion of the azeotropic vacuum distillation step, first toluene and then acetic ester (111 g after 4 hours corresponding to 1.26 moles) are distilled under normal pressure and at an internal flask temperature of 160° C. The solidified residue is further distilled in a high vacuum with 185 g (83.3% of the theoretical) of a colorless product which solidifies in the receiver and then melts at 121°–123° C., distilling over at 187°–193° C./0.03 Torr. Analysis by gas chromatography shows the product to be 97 to 98% pure.

Analytical data: $C_{12}H_{22}N_4$ (molecular weight: 222): calculated: C 64.9 H 10.0 N 25.2. observed: C 64.3 H 9.8 N 25.4.

EXAMPLE 2

Production of 1,6-bis-(2-methyl-tetrahydropyrimidinoyl-1)-hexane 147 g of 1,14-diamino-4,11-diazatetradecane (0.64 mole), 300 ml of toluene and 166.6 g of acetoacetic ester (1.28 moles) are combined and heated for 2 hours to a maximum of 40° C. under a pressure of 20 Torr. During that 2 hours, 23 g of water (100%) distill over and are separated off by means of an evacuable water separator. To remove the solvent and the acetic ester, the reaction mixture is heated for 4 hours to 160° C. The residue is distilled in a high vacuum with 161 g (90%) of a yellowish product which, according to analysis by gas chromatography, is 96 to 97% pure distilling over at 0.1 Torr and at a transition temperature of 225° to 245° C.

Analytical data: $C_{16}H_{30}N_4$ (molecular weight: 278): calculated: C 69.1 H 10.8 N 20.1. observed: C 68.4 H 10.8 N 19.7.

$n_D^{23}$: 1.5220.

Example 3

Production of 1,7-bis-(2-methyl-tetrahydropyrimidinoyl-1)-4-methyl-4-azaheptane 750 g of 1,15-diamino-8-methyl-4,8,12-triazatetradecane (2.9 moles), 753 g of acetoacetic ester (5.8 moles) and 800 ml of toluene are combined and heated for 3 hours to a maximum of 40° C. under a pressure of 20 Torr. During that time, 105 g of water (100%) distill over and are separated off from the reaction mixture by means of an evacuable water separator. Toluene and acetic ester are eliminated by distillation under normal pressure at a bath temperature of 140° C. The residue, which according to $^1$H-NMR is 90% pure, is distilled in a high vacuum. 736 g (83%) of a yellow-colored product which shows a correct $^1$H-NMR-spectrum distills over at 220°–240° C. under a pressure of 0.1 Torr and at a bath temperature of 260° to 280° C.

Analytical data: $C_{17}H_{33}N_5$ (molecular weight: 307): calculated: C 66.5 H 10.8 N 22.8. observed: C 66.1 H 11.3 N 22.3.

$n_D^{23}$: 1.5228.

Example 4

Production of 1,23-bis-(2-methyl-tetrahydropyrimidinoyl-1)-10,14-dimethyl-8,16-dioxo-9,12,15-trioxa-7,17-diaza-tricosane (idealized)

The starting amine used is a polyamine of the type obtained by reacting acrylonitrile with a diamine which was produced by hydrolysis of an NCO-prepolymer of 1,6-diisocyanatohexane and technical dipropylene glycol and which has an NH-number of 205. 197 g of 1,31-diamino-4,11,21,28-tetrazo-14,18-dimethyl-12,20-dioxo-13,16,19trioxa-pentriacontane(0.372 mole) thus produced, are mixed with 96.7 g (0.744 mole) of acetoacetic ester and 500 ml of toluene and the resulting mixture heated for 2 hours to 40° C. under a pressure of 20 Torr. During that time, 14 ml of water (100%) distill over and are removed from the equilibrium by means of an evacuable water separator. Toluene and acetic ester are distilled off at 140° C. and normal pressure and then at 100° C. and 0.1 Torr, leaving behind a pulp-like residue which is permeated by crystals melting at around 80° C. and of which the analytical data are as follows:

$C_{30}H_{56}N_6O_5$ (molecular weight: 590): calculated: C 61.0 H 9.5 N 14.2. observed: C 60.6 H 9.5 N 13.7.

Example 5

Production of 1-(3-di-N-methylaminopropyl)-2-methyl tetrahydropyrimidine 532 g of N,N-dimethyl-1,7-diamino-4-azaheptane (3.3 moles), 429 g of acetoacetic ester (3.3 moles) and 800 ml of toluene are heated for 2 hours to 40° C. under a pressure of 20 Torr, with 58.4 g of water (100%) being separated off. The toluene and acetic ester which accumulate are distilled off under normal pressure. Distillation in vacuo (0.02 Torr) gives 490 g (81%) of a colorless product having a boiling point of 103° C./0.02 Torr, a correct $^1$H-NMR-spectrum and the following analytical data:

$C_9H_{19}N_3$ (molecular weight: 183): calculated: C 59.0 H 10.4 N 23.0. observed: C 59.7 H 10.5 N 22.6.

$n_D^{23}$: 1.4906.

Example 6.

Production of 1,2-bis-(2-methyl-tetrahydropyrimidinoyl-1)-ethane-bis-(hydrogen carbonate)

22.2 g of 1,2-bis-(2-methyl-tetrahydropyrimidinoyl-1)-ethane (0.1 mole) and 3.6 g of water (0.2 mole) are dissolved in 300 ml of methanol, and $CO_2$ is introduced to saturation level at 0° C. to 10° C. The crystals precipitated are filtered off under suction and dried melt at 138° to 140° C. Yield: 31.6 g (91% of the theoretical).

Analytical data: $C_{18}H_{34}N_4O_6$ (molecular weight: 346): calculated: C 48.5 H 7.5 N 15.6. observed. C 49.0 H 8.0 N 15.8.

Example 7

Production of 1,2-bis-(2-methyl-tetrahydropyrimidinoyl-1)-ethane-bis-(phenolate)

11.1 g of 1,2-bis-(2-methyl-tetrahydropyrimidinoyl-1)-ethane (50 mMoles) and 9.4 g of phenol (0.1 mole) are dissolved in 150 ml of acetone. After stirring for 2 hours, the acetone is distilled off, leaving behind 20.5 g (100%) of a highly viscous liquid which solidifies after a few days into crystals melting at 25° to 30° C.

Examples of the production of polyurethane plastics

The following starting compounds and catalysts are employed in the subsequent examples.

Isocyanates

Isocyanate A: a semiprepolymer of 4,4'-diisocyanatodiphenyl methane and tripropylene glycol having an NCO-value of 22.8%.

Isocyanate B: a semiprepolymer of isophorone diisocyanate and a glycerol-started polypropylene glycol ether having an OH-number of 670 having an NCO-value of 28%.

Isocyanate C: a mixture of 80 parts by weight of 2,4-tolylene diisocyanate and 20 parts by weight of 2,6-tolylene diisocyanate having an NCO-value of 48%.

Isocyanate D: a phosgenation product of aniline-formaldehyde condensates which has a viscosity of 130 mPas at 25° C. and an NCO-value of 31%.

Polyols

Polyol A: a trifunctional trimethylolpropane-started PO/EO-polyether polyol (with 22% b.w. EO) having an OH-number of 27 and an average molecular weight of 6222.

Polyol B: a difunctional propylene-glycol-started PO/EO-polyether polyol (with 20% b.w. EO) having an OH-number of 28 and an average molecular weight of 4000.

Polyol C: a trifunctional trimethylolpropane-started PO/EO-polyether polyol (with 15% b. w. EO) having an OH-number of 35 and an average molecular weight of 4500.

Polyol D: a polyol mixture having an average OH-number of 500 and a water content of less than 0.3% by weight and a viscosity at 25° C. of 2500 mPas consisting of (1) 60% by weight of a polyether having an OH-number of 860 obtained by the addition of propylene glycol with trimethylol propane and
(2) 40% by weight of polyether having an OH-number of 42 obtained by the addition of a mixture of propylene oxide and ethylene oxide with a mixture of trimethylol propane and propylene glycol (molar ratio 3:1).

Tetrahydropyrimidine catalysts

Catalyst A: 1,2-bis-(2-methyl-tetrahydropyrimidinoyl-1)-ethane of Example 1, corresponding to the following formula

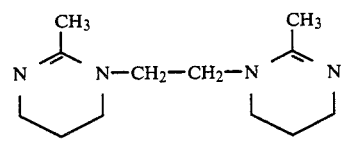

Catalyst B: 1,2-bis-(2-methyl-tetrahydropyrimidinoyl-1)-ethane-bis-(hydrogen carbonate) of Example 6.

Catalyst C: 1,2-bis-(2-methyl-tetrahydropyrimidinoyl-1)-ethane-bis-(phenolate) of Example 7.

Catalyst D: 1,6-bis-(2-methyl-tetrahydropyrimidinoyl-1)-hexane of Example 2, corresponding to the following formula

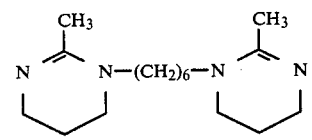

Catalyst E: 1,7-bis-(2-methyl-tetrahydropyrimidinoyl-1)-4-methyl-4-azaheptane of Example 3, corresponding to the following general formula

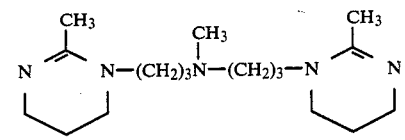

Catalyst F: 1,23-bis-(2-methyl-tetrahydropyrimidinoyl-1)-10,14-dimethyl-8,16-dioxo-7,17diaza-9,12,15-trioxatricosane of Example 4 corresponding to the following idealized formula

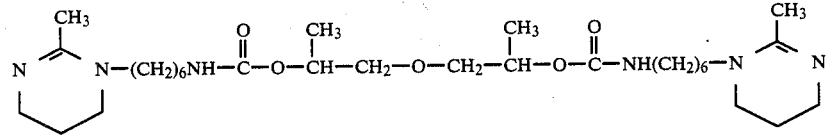

Catalyst G: 1-(3-di-N-methylaminopropyl)-2-methyl-tetrahydropyrimidine of Example 5 corresonding to the following formula

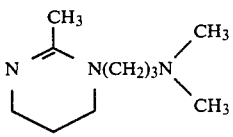

Catalyst H: 1,2-bis-(2-methyl-tetrahydropyrimidinoyl-1)-ethane-bis-(2-ethylhexanoate).

Catalyst I: 1,2-bis-(2-methyl-tetrahydropyrimidinoyl-1)-ethane-bis-(acetate).

The reaction times quoted are defined as follows:

$T_1$ = cream time (time in seconds after the isocyanate component has been stirred in, at which the mixture begins to foam);

$T_2$ = rise time (time in seconds after the isocyanate component has been stirred in, after which the rising process is over);

$T_3$ = tack-free time (time in seconds after the isocyanate component has been stirred in, at which the surface of the foam is no longer tacky);

$T_4$ = plucking time (time in seconds after the isocyanate component has been stirred in, at which small fragments can no longer be torn out of the foam with the fingers).

Production of Polyurethane Foam

Example 8

Semi-rigid integral skin polyurethane foams based on aliphatic isocyanates are produced from the following formulation.

Formulation:
1. 80 g of polyol A
2. 7 g of ethylene glycol
3. 0.5 g of dibutyl tin dilaurate
4. 12 g of trichlorofluoromethane
5. x g of amidine-based co-catalyst.

Components 1 to 5 above are carefully mixed for 30 secs. at room temperature using a high-speed stirrer, after which 41 g of isocyanate B are added and stirring continued for another 10 seconds. The mass is foamed in small open packs.

The times obtained are set out in Table 1.

TABLE 1

| | Data of Example 8 | | |
|---|---|---|---|
| Catalyst | Quantity (g) x | Times $T_1$ | (sec.) $T_4$ |
| Catalyst B | 1.2 | 43 ± 5 | 128 ± 10 |
| Catalyst C | 0.8 | 46 ± 5 | 110 ± 10 |
| Catalyst D | 0.4 | 19 ± 3 | 98 ± 10 |
| | 0.8 | 10 ± 1 | 55 ± 5 |
| Catalyst E | 0.4 | 21 ± 3 | 122 ± 10 |
| | 0.6 | 14 ± 1 | 95 ± 10 |
| Catalyst G | 0.4 | 22 ± 3 | 97 ± 10 |
| | 0.6 | 17 ± 3 | 69 ± 5 |
| Diazabicycloundecene (for comparison) | 0.4 | 25 ± 3 | 103 ± 10 |

Example 9

Semi-rigid integral skin polyurethane foams based on aromatic isocyanates are produced from the following formulation.

Formulation:
1. 70 g of polyol B
2. 20 g of polyol C
3. 1 g of ethylene glycol
4. 14 g of 1,4-butane diol
5. 0.1 g of water
6. 10 g of trichlorofluoromethane
7. 0.02 g of dibutyl tin dilaurate
8. x g of amidine-based co-catalyst.

The above components are carefully mixed for 30 seconds at room temperature using a high-speed stirrer, after which 74 g of isocyanate A are added and stirring is continued for another 10 seconds. The mass is foamed in small open packs.

The times obtained are shown in Table 2.

TABLE 2

| | Data of Example 9 | | | | |
|---|---|---|---|---|---|
| | Quantity | Times (seconds) | | | |
| Catalyst | (g) x | $T_1$ | $T_2$ | $T_3$ | $T_4$ |
| Catalyst A | 0.8 | 15 ± 1 | 27 ± 3 | 27 ± 3 | 27 ± 3 |
| Catalyst B | 1.2 | 38 ± 3 | 58 ± 5 | 58 ± 5 | 62 ± 5 |
| | 1.8 | 28 ± 3 | 53 ± 5 | 53 ± 5 | 57 ± 5 |
| Catalyst C | 0.8 | 23 ± 3 | 35 ± 3 | 35 ± 3 | 37 ± 3 |
| | 1.2 | 16 ± 1 | 27 ± 3 | 27 ± 3 | 32 ± 3 |
| Catalyst D | 0.3 | 23 ± 3 | 32 ± 3 | 35 ± 3 | 35 ± 3 |
| | 0.15 | 30 ± 3 | 37 ± 3 | 42 ± 3 | 42 ± 3 |
| Catalyst E | 0.3 | 23 ± 3 | 35 ± 3 | 36 ± 3 | 36 ± 3 |
| | 0.15 | 25 ± 3 | 40 ± 5 | 44 ± 5 | 51 ± 5 |
| Catalyst G | 0.3 | 24 ± 3 | 33 ± 3 | 37 ± 3 | 37 ± 3 |
| | 0.15 | 27 ± 3 | 42 ± 5 | 48 ± 5 | 48 ± 5 |
| Triethylenediamine (DABCO ®) (for comparison) | 0.3 | 25 ± 3 | 38 ± 3 | 50 ± 5 | 62 ± 5 |

Example 10

Flexible Polyurethane Foams are produced from the following formulation.

Formulation:
1. 50 g of polyol C
2. 1.5 g of water
3. 0.5 g of a commercial polysiloxane/polyalkylene oxide block polymer as foam stabilizer (OS 50 of Goldschmidt AG, Germany)
4. 0.05 g of tin dioctoate
5. x g of amidine catalyst The above components are mixed with one another for 30 seconds at room temperature using a high-speed stirrer, after which 18 g of isocyanate C are added and mixing is continued for another 5 seconds. The mass is foamed in small open packs. The times in question ($T_1$ = cream time, $T_2$ = rise time) are shown in Table 3.

TABLE 3

| Catalyst (0.3 g) | Cream time (sec. ±3) | Rise time (sec. ±5) |
|---|---|---|
| Catalyst D | 13 | 79 |
| Catalyst E | 13 | 98 |
| Catalyst G | 10 | 73 |
| Comparison a | 14 | 62 | a Commercial amine-containing flexible foam catalyst (Desmorapid ® PS 207 of Bayer AG, Germany).

Example 11a (Comparison Example)

Rigid integral skin polyurethane foam is produced in the following examples.

Formulation (Component A):
1. 100 g of polyol D
2. 1 g of a commercial polysiloxane/polyalkylene oxide block copolymer as foam stabilizer according to Example 10
3. 3 g of N-dimethyl benzylamine
4. 0.5 g of tetramethyl guanidine 5. 3.0 g of amide amine produced from 1 mole of 3-dimethyl amino-1-propylamine and 2 moles of oleic acid as internal release agent
6. 0.2 g of 85% aqueous orthophosphoric acid as reaction retarder and
7. 10 g of trichloromonofluoromethane as blowing agent are mixed with one another for 30 seconds at room temperature using a high-speed stirrer. Isocyanate D is then added to 100 g of the above mixture, mixing is continued for another 10 seconds using a high-speed stirrer and the mass is then immediately poured into an open paper mold (dimensions: 250×120×120 mm). The following reaction times are obtained:
cream time: 24±3 sec.
gel time: 42±5 sec.

Example 11b

Formulation:
1. 10 g of polyol D
2. 1 g of foam stabilizer (same as in Example 10 )
3. 3 g of amide amine (same as in Example 11a)
4 x g of amidine catalyst
5. 10 g of trichloromonofluoromethane
6. 1 g of isocyanate D.

The procedure is as in Example 11a. The reaction times obtained are shown in Table 4.

Example 11c

In this test series, 0.2 g of 85% aqueous orthophosphoric acid is added as reaction retarder to the polyol mixture before it is mixed with the amidine catalyst. The reaction times obtained are shown in Table 5.

TABLE 4

| Catalyst | Quantity of catalyst (g/moles) | Cream time (sec.) | Gel time (sec.) |
|---|---|---|---|
| Catalyst A | 0.9 g/4.05 mMoles | 29 ± 3 | 38 ± 3 |
|  | 1.0 g/4.50 mMoles | 23 ± 3 | 33 ± 3 |
|  | 1.1 g/4.95 mMoles | 19 ± 3 | 28 ± 3 |
| Catalyst B | 1.6 g/4.5 mMoles | 35 ± 3 | 65 ± 5 |
|  | 1.9 g/5.5 mMoles | 30 ± 3 | 50 ± 5 |
|  | 2.4 g/6.9 mMoles | 26 ± 3 | 42 ± 5 |
| Catalyst C | 1.85 g/4.5 mMoles | 21 ± 3 | 28 ± 3 |
|  | 1.7 g/4.15 mMoles | 25 ± 3 | 44 ± 5 |
| Catalyst D | 1.25 g/4.5 mMoles | 14 ± 3 | 18 ± 3 |
|  | 0.9 g/3.24 mMoles | 22 ± 3 | 27 ± 3 |
|  | 0.85 g/3.06 mMoles | 25 ± 3 | 30 ± 3 |
| Catalyst E | 1.38 g/4.5 mMoles | 14 ± 3 | 19 ± 3 |
|  | 1 g/3.25 mMoles | 22 ± 3 | 26 ± 3 |
|  | 0.9 g/2.93 mMoles | 24 ± 3 | 29 ± 3 |
| Catalyst F | 2.6 g/4.5 mMoles | 45 ± 5 | 75 ± 5 |
|  | 7 g/12.07 mMoles | 40 ± 5 | 110 ± 10 |
| Catalyst G | 0.82 g/4.5 mMoles | 24 ± 3 | 32 ± 3 |
| For Comparison |  |  |  |
| 2.5 g of dimethyl benzylamine 0.3 g of tetramethyl guanidine |  | 24 ± 3 | 37 ± 3 |
| 3 g of dimethyl benzylamine 0.5 g of tetramethyl guanidine |  | 19 ± 3 | 27 ± 3 |
| 2.5 g of dimethyl benzylamine 0.25 g of tetramethyl guanidine |  | 24 ± 3 | 43 ± 5 |

TABLE 5

| Catalyst | Quantity (g/moles) x | Cream time (sec.) | Gel time (sec.) |
|---|---|---|---|
| Catalyst A | 1.3 g/5.9 mMoles | 32 ± 3 | 52 ± 5 |
|  | 1.5 g/6.76 mMoles | 24 ± 3 | 38 ± 3 |
|  | 1.6 g/7.21 mMoles | 21 ± 3 | 32 ± 3 |
| Catalyst B | 2.3 g/6.76 mMoles | 55 ± 5 | 115 ± 10 |
|  | 3 g/8.67 mMoles | 35 ± 3 | 80 ± 5 |
|  | 3.5 g/10.12 mMoles | 25 ± 3 | 45 ± 5 |
| Catalyst C | 2.77 g/6.76 mMoles | 50 ± 5 | 90 ± 10 |
|  | 3.5 g/8.54 mMoles | 23 ± 3 | 32 ± 5 |

TABLE 5-continued

| Catalyst | Quantity (g/moles) x | Cream time (sec.) | Gel time (sec.) |
|---|---|---|---|
|  | 4.0 g/9.67 mMoles | 17 ± 3 | 23 ± 5 |
| Catalyst D | 1.2 g/4.32 mMoles | 32 ± 3 | 41 ± 3 |
|  | 1.35 g/4.86 mMoles | 25 ± 3 | 34 ± 3 |
|  | 1.5 g/5.4 mMoles | 20 ± 3 | 25 ± 3 |
|  | 1.9 g/6.76 mMoles | 18 ± 3 | 22 ± 3 |
| Catalyst E | 1.5 g/4.89 mMoles | 25 ± 3 | 34 ± 3 |
|  | 1.8 g/5.87 mMoles | 18 ± 3 | 23 ± 3 |
|  | 2.07 g/6.76 mMoles | 16 ± 3 | 22 ± 3 |
| Catalyst F | 3.92 g/6.76 mMoles | 75 ± 5 | 170 ± 15 |
|  | 7.6 g/13.1 mMoles | 70 ± 5 | 150 ± 15 |
| Catalyst G | 1.24 g/6.76 mMoles | 32 ± 3 | 43 ± 5 |
|  | 1.5 g/8.2 mMoles | 24 ± 3 | 33 ± 3 |

Example 12

Semi-rigid integral skin polyurethane foam is produced in the following example.

This example demonstrates the self-blowing effect of catalyst B.

Formulation
1. 70 g of polyol B
2. 20 g of polyol C
3. 1 g of ethylene glycol
4. 14 g of 1,4-butane diol
5. 1 g of catalyst B The components are carefully stirred for 30 seconds at room temperature using a high-speed mixer, after which 74 g of isocyanate A are added, the mixture stirred for another 10 seconds using a high-speed stirrer and subsequently foamed in a paper mold. The following data are obtained: $T_1 = 20$ sec.±3; $T_2$, $T_3$, $T_4 = 40$ sec.±3.

The free rise foam density amounts to 0.35 kg/m$^3$.

What is claimed is:

1. Tetrahydropyrimidines corresponding to the formula

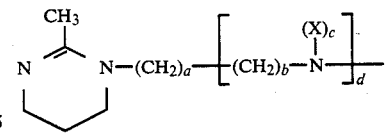

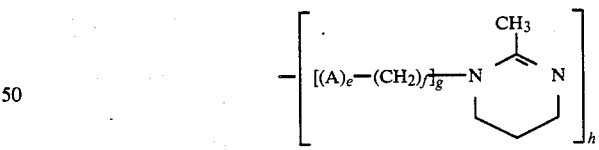

wherein

A is a divalent straight-chain or branched-chain $C_1$–$C_{17}$-alkylene or $C_5$–$C_{10}$-cycloalkylene radical which may be interrupted in the chain by —NH—COO—, —O— and/or —S—; or a $C_1$–$C_4$-alkylene bis(cyclohexyl) radical which may be substituted by a phenyl or halogen radical or a cyano group; or a dicyclohexyl radical;

X is a monovalent straight-chain or branched-chain $C_1$–$C_{16}$-alkyl radical; a $C_5$–$C_7$-cycloalkyl radical which may be substituted by a phenyl or halogen radical or a cyano or hydroxy group; or, where h=0, together with N may form a ring consisting of 3 to 6 ring-C-atoms of which one or two C-atoms may be replaced by —O—, —S—, —NH— or —NR³— where R³ represents a $C_1$-$C_6$-alkyl or ω-hydroxy-$C_1$-$C_6$-alkyl;

a=0 or an integer of from 1 to 16;

b=an integer of from 1 to 16, but if d=0, then b must=0;

c=1 or 2, but if d=0, then c must=0;

d=0 or an integer of from 1 to 10;

e=0 or 1, but if g=0, then e must=0;

f=0 or an integer of from 1 to 16, but if g=0, then f must=0;

g=an integer 1 to 16, but if h=0, then g must=0;

h=0 or 1, but if d≧1, then h+c must=2; and d and h cannot both =0.

2. Tetrahydropyrimidines according to claim 1 wherein

A is a divalent straight-chain or branched-chain $C_1$-$C_{17}$-alkylene or $C_5$-$C_{10}$-cycloalkylene radical which may be interrupted in the chain by —NH—COO—, —O— and/or —S—; or a $C_1$-$C_4$-alkylene bis(cyclohexyl) radical which may be substituted by a phenyl or halogen radical or a cyano group;

X is a monovalent straight-chain or branched-chain $C_1$-$C_{16}$-alkyl radical: a $C_5$-$C_7$-cycloalkyl radical which may be substituted by a phenyl or halogen radical or a cyano or hydroxy group; or, where h=0, together with N may form a ring consisting of 3 to 6 ring-C-atoms of which one or two C-atoms may be replaced by —O—, —S—, —NH— or —NR³— where R³ represents a $C_1$-$C_6$-alkyl or ω-hydroxy-$C_1$-$C_6$-alkyl;

a=an integer of from 1 to 16;

b=an integer of from 1 to 16, but if d=0, then b must=0;

c=1 or 2, if d=0, then c must=0;

d=0 or an integer of from 1 to 10;

e=0 or 1, but if g=0, then e must=0;

f=an integer of from 1 to 16, but if g=0, then f must=0;

g=an integer of from 1 to 16, but if h=0, then g must=0;

h=0 or 1, but if d≧1, then h+c must=2; and d and h cannot both=0.

3. Tetrahydropyrimidines corresponding to the formula

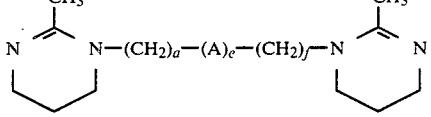

wherein

A is a divalent straight-chain or branched-chain $C_1$-$C_{17}$-alkylene or $C_5$-$C_{10}$-cycloalkylene radical which may be interrupted in the chain by —NH—COO—, —O— and/or —S—; or a $C_1$—$C_4$-alkylene bis(cyclohexyl) radical which may be substituted by a phenyl or halogen radical or a cyano group; or a dicyclohexyl radical;

a and f are 0 or integers of from 1 to 16; and e is 0 or 1.

4. Tetrahydropyrimidines according to claim 2 wherein

A is a divalent straight-chain or branched-chain $C_1$-$C_{17}$-alkylene or $C_5$-$C_{10}$-cycloalkylene radical which may be interrupted in the chain by —NH—COO—, —O— and/or —S—; or a $C_1$-$C_4$-alkylene bis(cyclohexyl) radical which may be substituted by a phenyl or halogen radical or a cyano group;

a and f are integers of from 1 to 16; and e is 0 or 1.

5. Tetrahydropyrimidines corresponding to the formula

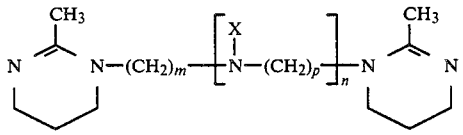

wherein

X represents a straight-chain or branched-chain $C_1$-$C_{16}$-alkyl radical or a $C_5$-$C_7$-cycloalkyl radical which may be substituted by a phenyl radical, a cyano group or a halogen radical;

m and p are integers of from 2 to 10; and n is an integer of from 1 to 16.

6. Tetrahydropyrimidines according to claim 1 or claim 2 or claim 3 or claim 4 or claim 5 in the form of their salts, addition compounds and complexes with Lewis acids and proton acids.

* * * * *